United States Patent
Norton et al.

(10) Patent No.: US 7,544,326 B2
(45) Date of Patent: *Jun. 9, 2009

(54) FIXED MOUNTED SORTING CUVETTE WITH USER REPLACEABLE NOZZLE

(75) Inventors: Pierce O. Norton, Morgan Hill, CA (US); David R. Vrane, San Jose, CA (US); Shervin Javadi, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/711,320

(22) Filed: Feb. 26, 2007

(65) Prior Publication Data

US 2007/0148043 A1    Jun. 28, 2007

(51) Int. Cl.
  *G01N 33/00*    (2006.01)
(52) U.S. Cl. .................. 422/73; 422/82.05; 422/82.09; 422/102; 356/335; 356/336; 356/337; 356/338; 356/441; 356/442
(58) Field of Classification Search ............... 422/68.1, 422/73, 82.05, 82.08, 82.09, 99, 100, 102; 356/335, 336, 337, 338, 441, 442
See application file for complete search history.

(56) References Cited

U.S. PATENT DOCUMENTS

| | | |
|---|---|---|
| 4,412,466 A | 11/1983 | Jurkowski et al. |
| 4,515,274 A | 5/1985 | Hollinger et al. |
| 4,660,971 A | 4/1987 | Sage et al. |
| 5,007,732 A | 4/1991 | Ohki et al. |
| 5,159,403 A | 10/1992 | Kosaka |
| 5,517,870 A | 5/1996 | Kurimura |
| 5,521,699 A | 5/1996 | Kosaka et al. |
| 5,594,545 A | 1/1997 | Saito et al. |
| 5,602,039 A | 2/1997 | Van den Engh |
| 5,606,412 A | 2/1997 | Saito et al. |
| 5,684,575 A | 11/1997 | Steen |
| 5,700,692 A | 12/1997 | Sweet |
| 5,726,364 A | 3/1998 | Van den Engh |
| 5,819,948 A | 10/1998 | Van den Engh |
| 5,973,842 A | 10/1999 | Spangenberg |

(Continued)

FOREIGN PATENT DOCUMENTS

JP    2095241 A2    4/1990

OTHER PUBLICATIONS

Chaudhary, K. C. et al., "The Nonlinear Capilary Instability of a Liquid Jet. Part 2: Theory", J. Fluid. Mech., vol. 96 (1980a).

(Continued)

*Primary Examiner*—Jill Warden
*Assistant Examiner*—Dwayne K Handy
(74) *Attorney, Agent, or Firm*—Douglas A. Petry

(57) ABSTRACT

A flow cell and flow cytometer in which a nozzle at the end of a flow channel is disposed on a removable substrate held at a registered location on a flow cell. Other elements including illumination optics, light collection optics, and the flow cell may then be positioned at fixed locations and would not require subsequent periodic adjustment. The registered location for positioning the nozzle allows removal and replacement of the nozzle key with the nozzle subsequently positioned in the identical location.

9 Claims, 9 Drawing Sheets

U.S. PATENT DOCUMENTS

| | | |
|---|---|---|
| 5,998,212 A | 12/1999 | Corio et al. |
| 6,042,249 A | 3/2000 | Spangenberg |
| 6,079,836 A | 6/2000 | Burr et al. |
| 6,133,044 A | 10/2000 | Van den Engh |
| 6,248,590 B1 | 6/2001 | Malachowski |
| 6,263,745 B1 | 7/2001 | Buchanan et al. |
| 6,281,018 B1 | 8/2001 | Kirouac et al. |
| 6,357,307 B2 | 3/2002 | Buchanan et al. |
| 6,372,506 B1 | 4/2002 | Norton |
| 6,710,874 B2 | 3/2004 | Mavliev |
| 7,201,875 B2 * | 4/2007 | Norton et al. ......... 422/73 |

OTHER PUBLICATIONS

Chaudhary, K. C. et al., "The Nonlinear Capilary Istability of a Liquid Jet. Part 2: Experiments on Jet Behaviour before Droplet Formation", J. Fluid. Mech., vol. 96 (1980b).

Chaudhary, K. C. et al., "The Nonlinear Capilary Instability of a Liquid Jet. Part 3: Experiments on Satellite Droplet Formation and Control", J. Fluid. Mech., vol. 96 (1980a).

Lord Rayleigh, "On the Instability of Jets", Proc. London Math. Society, vol. 10, 1978, pp. 4-13.

Practical Flow Cytometry, 3-rd Edition, Howard M. Sapiro, Wiley & Sons, Inc., New york 1995.

* cited by examiner

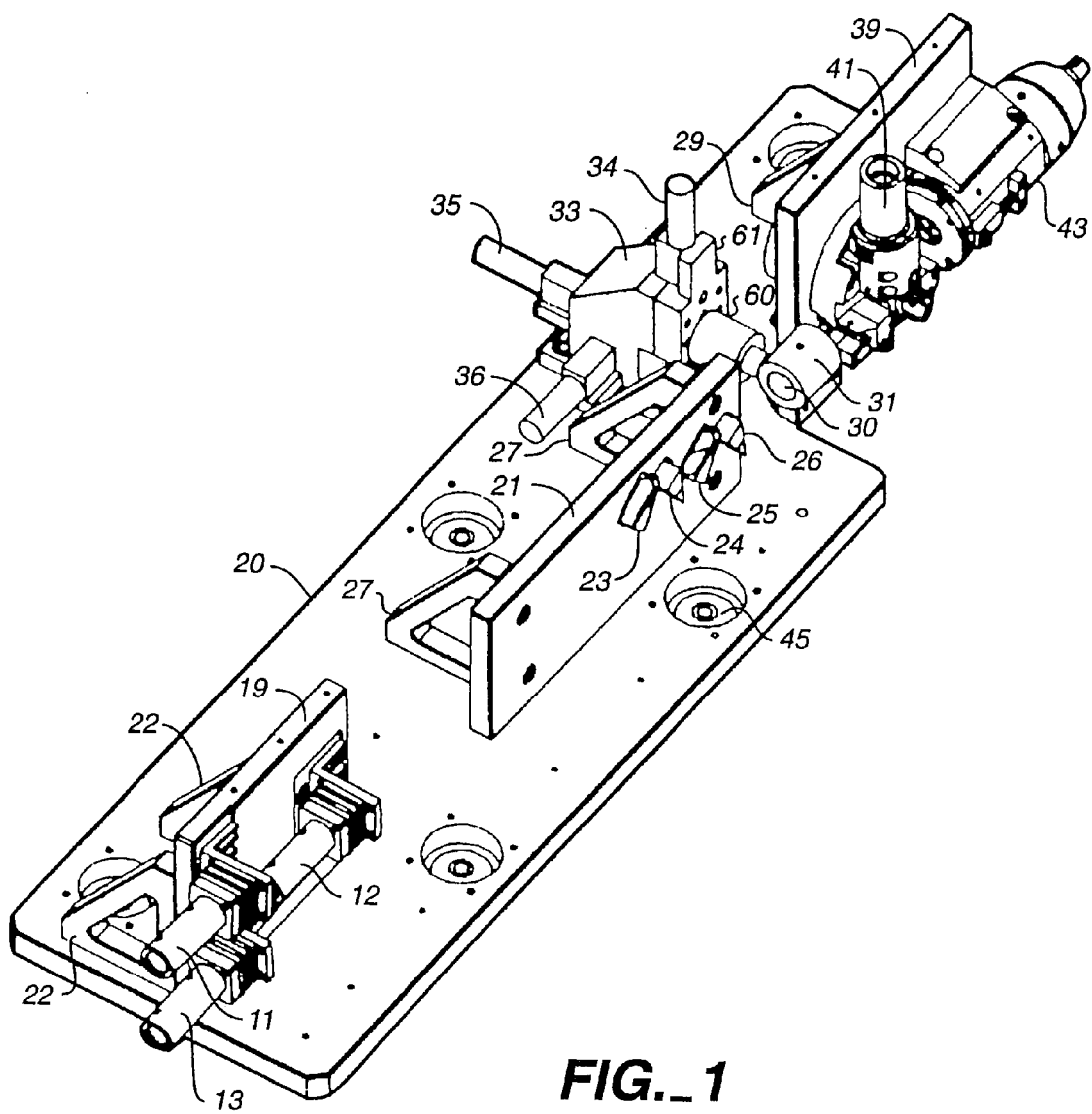
FIG._1

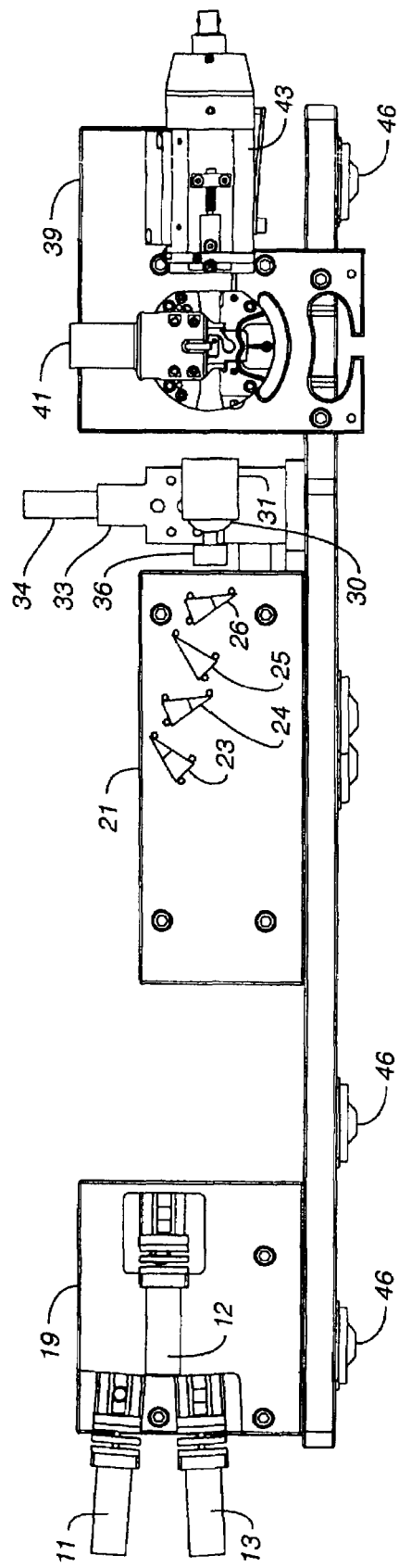
FIG._2

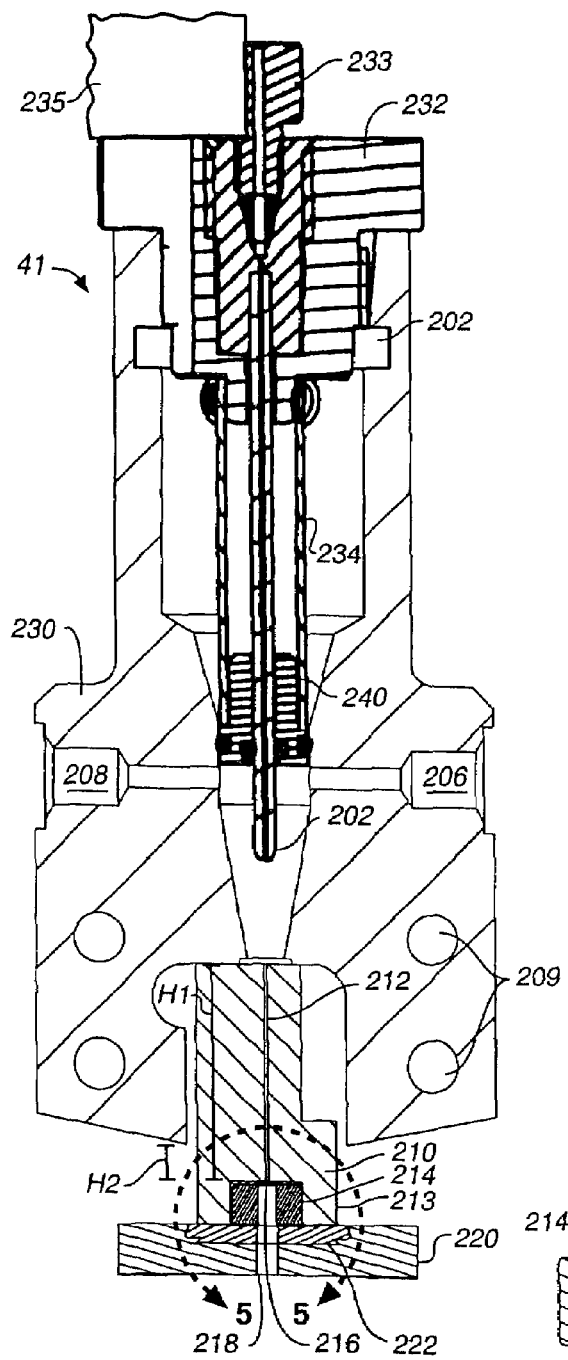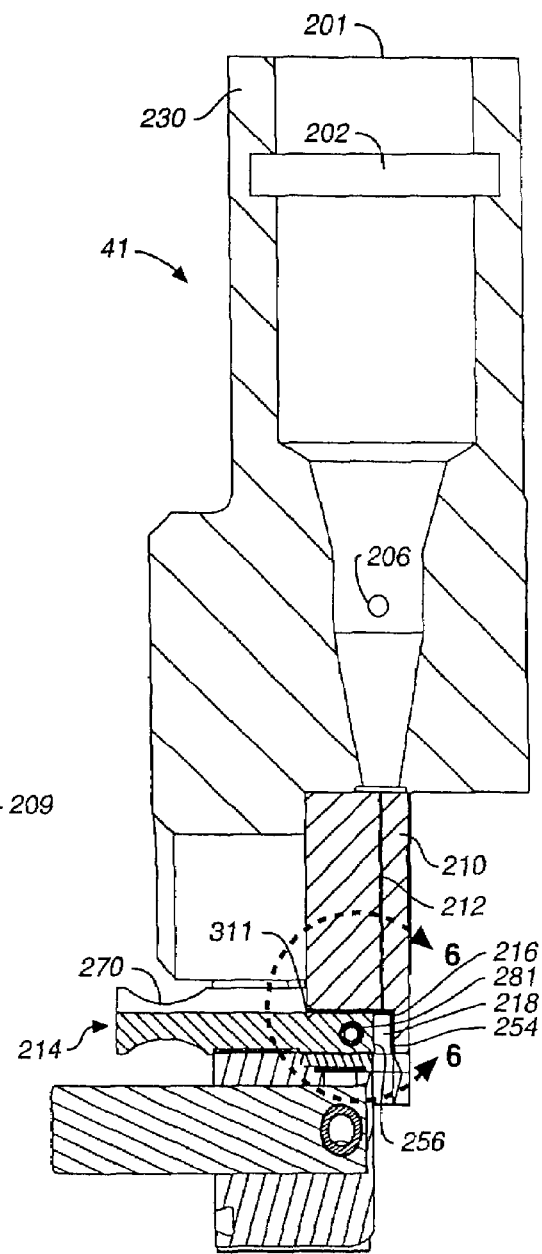
FIG._3    FIG._4

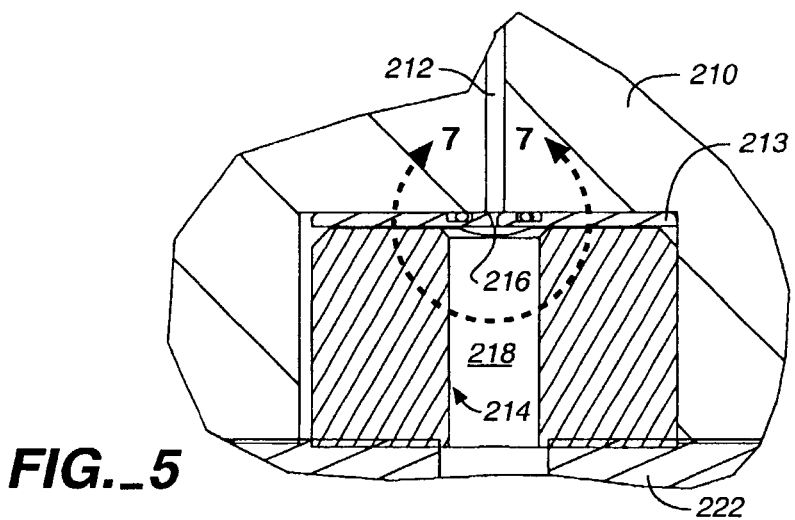
FIG._5
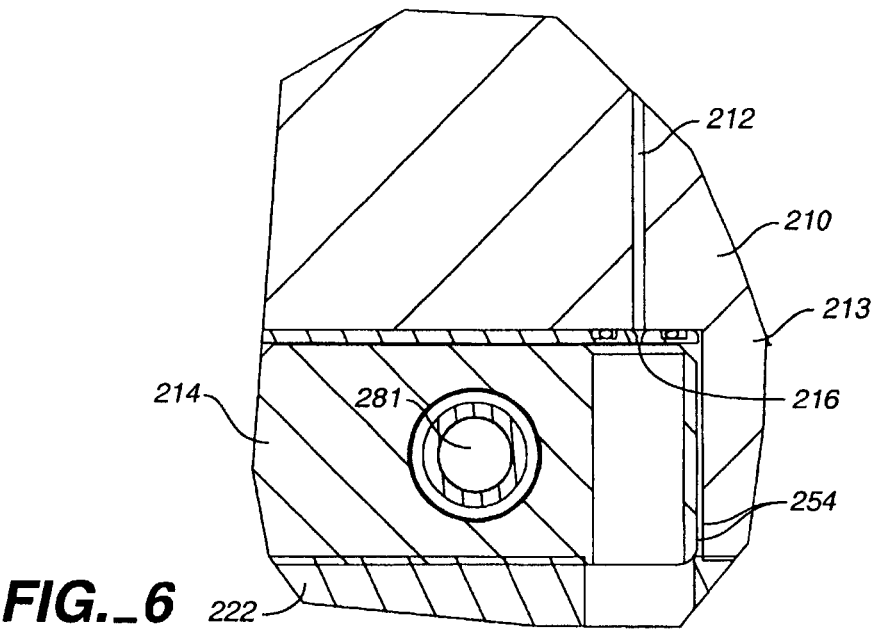
FIG._6
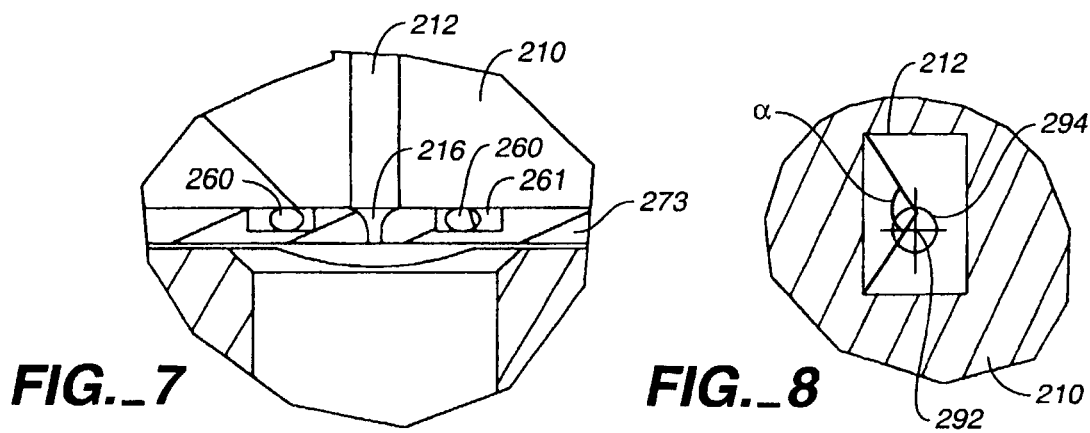
FIG._7
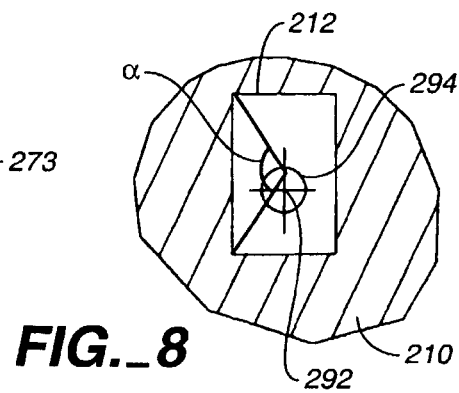
FIG._8

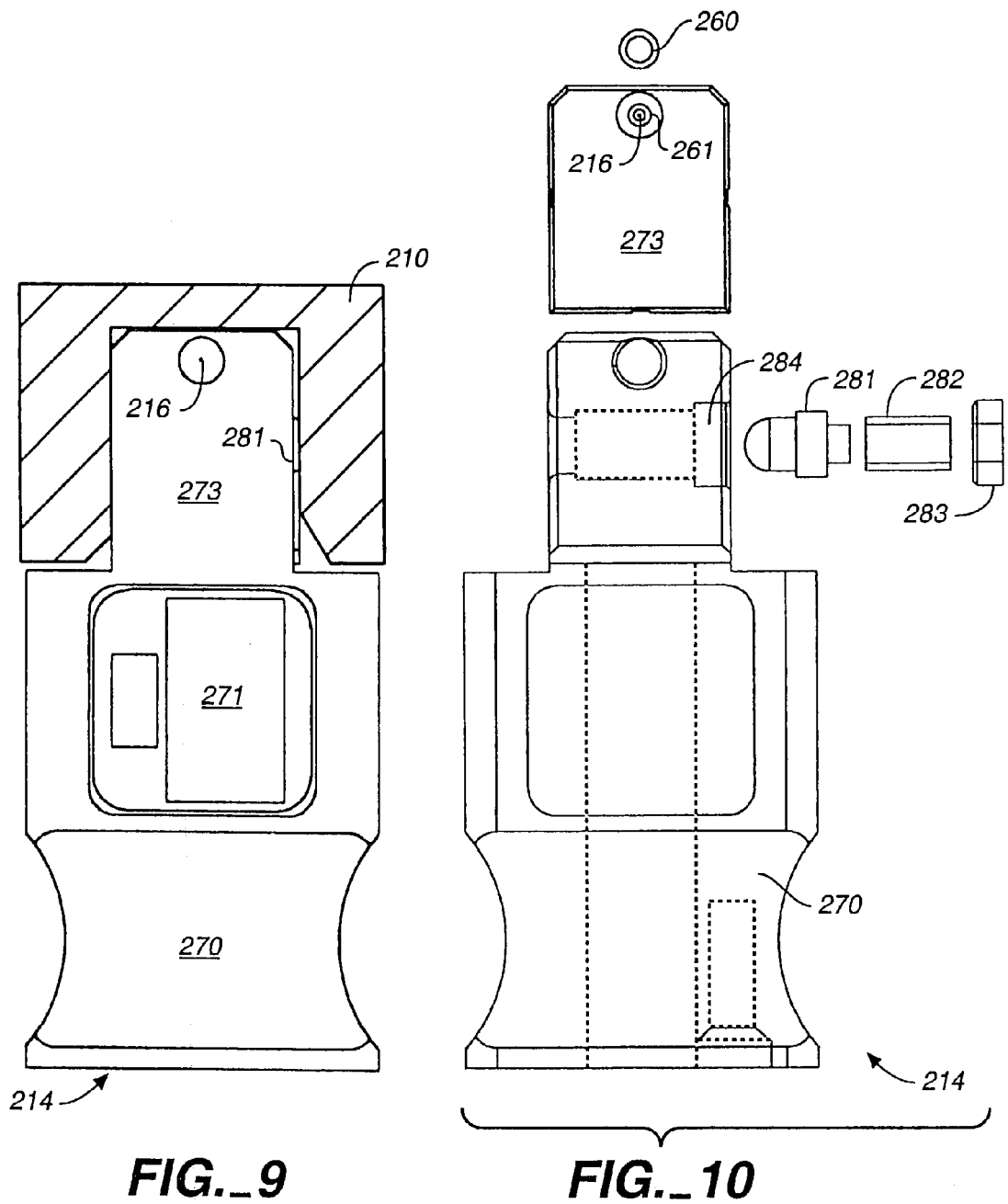

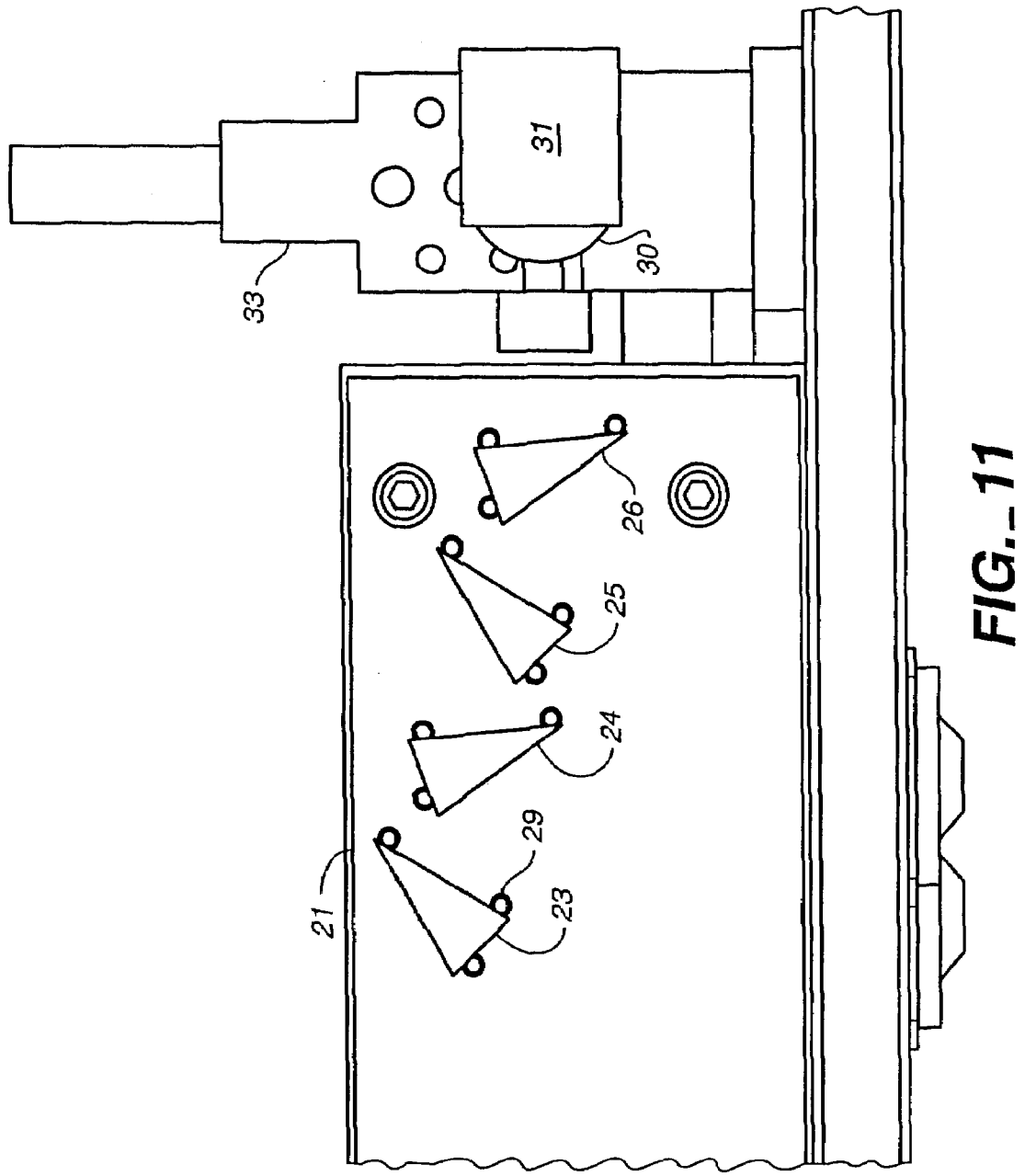
FIG._11

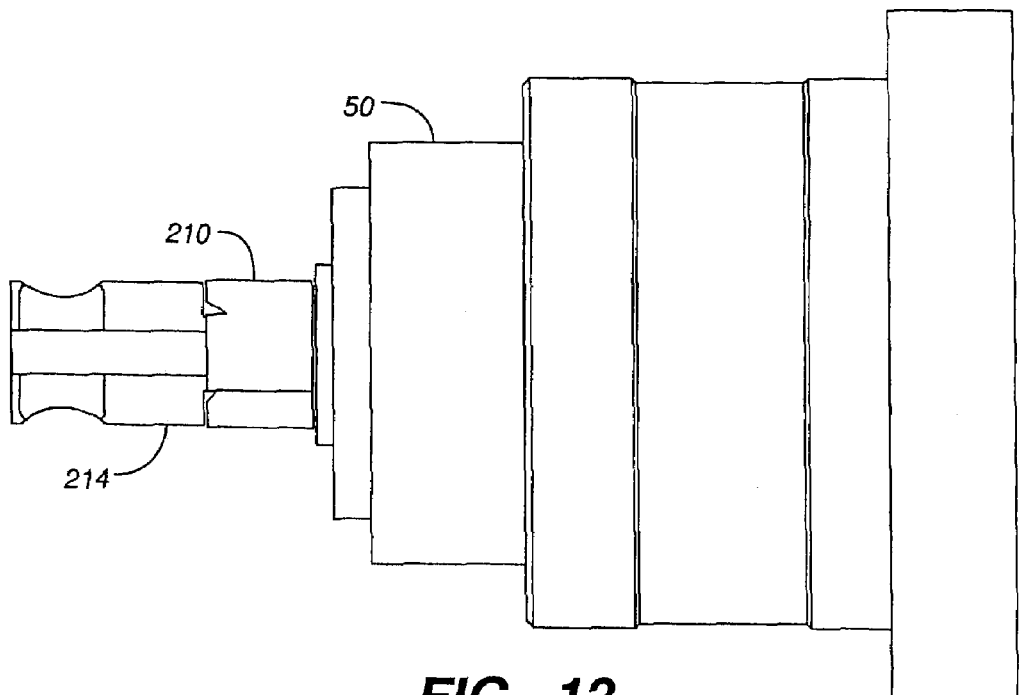
FIG._12
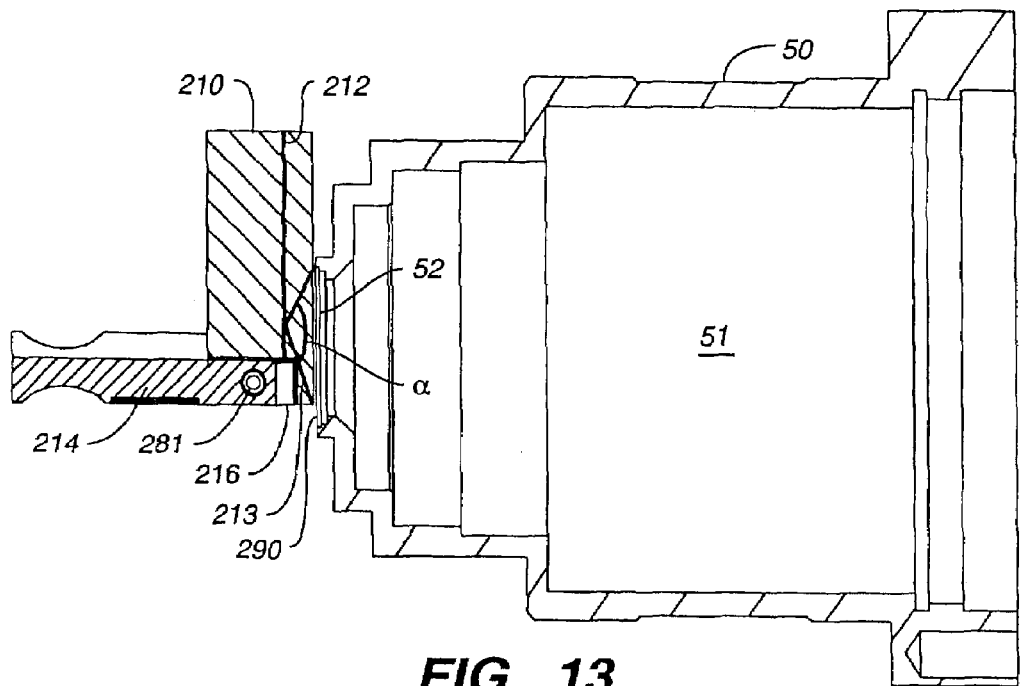
FIG._13

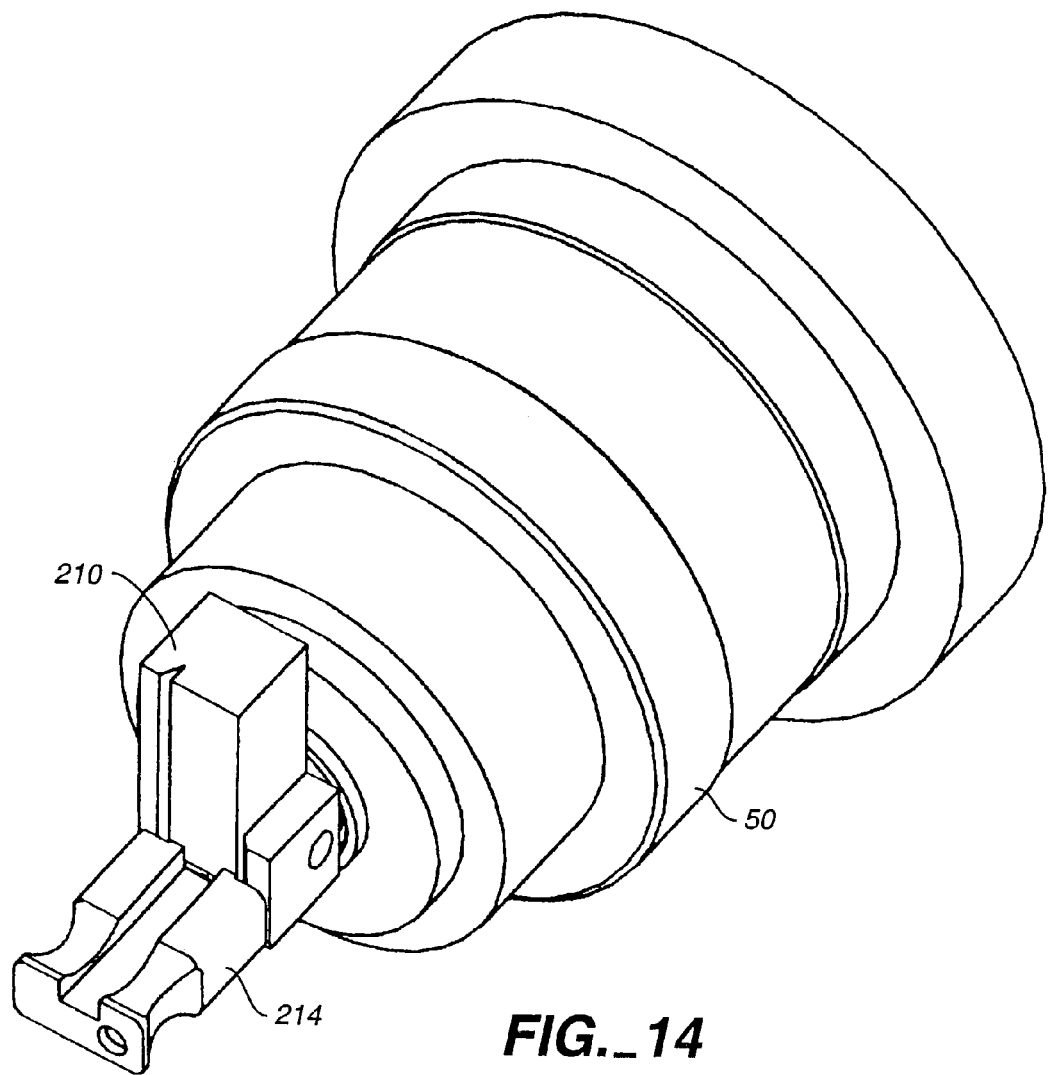
FIG._14

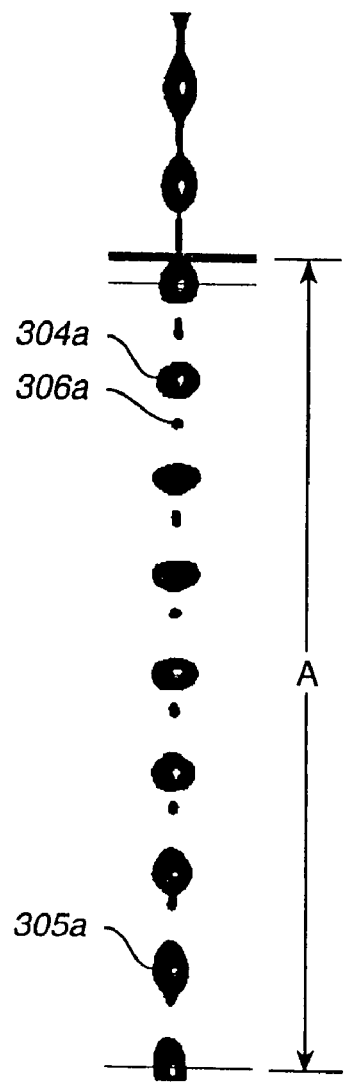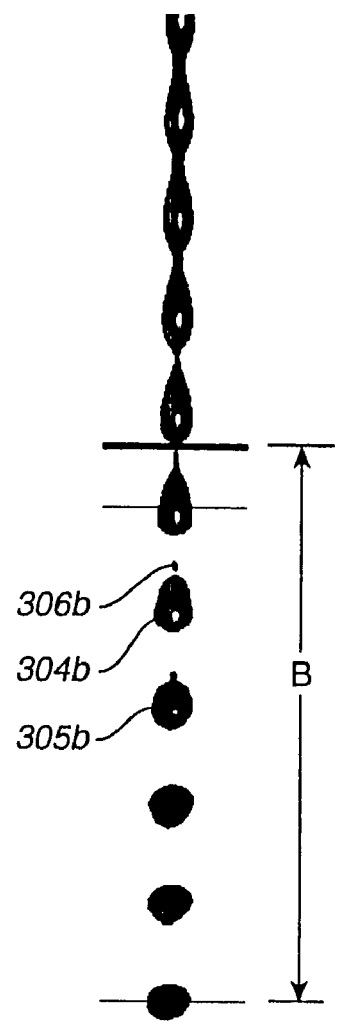
FIG._15A  FIG._15B

FIXED MOUNTED SORTING CUVETTE WITH USER REPLACEABLE NOZZLE

CROSS-REFERENCE TO RELATED APPLICATIONS

The present application claims priority to U.S. application Ser. No. 10/259,332, filed Sep. 27, 2002, which is incorporated herein by reference in its entirety.

TECHNICAL FIELD

The present invention relates to flow cytometry.

BACKGROUND OF THE INVENTION

Flow analysis has proven to be an important technology for the analysis of discrete targets. The applications of this technology include cellular assay to investigate a variety of cellular features including DNA content, specific nucleic acid sequences, chromatic structure, RNA content, specific antigens, surface receptors, cell morphology, DNA degredation and other assay targets. The targets of a flow cytometer may be multicellular organisms (e.g. microfilaria), cellular aggregates, viable cells, dead cells, cell fragments, organelles, large molecules (e.g. DNA), particles such as beads, viral particles or other discrete targets of this size range. The term "cells", as used throughout, is used to refer to such discrete targets. This technology has a number of different applications, including diagnostic, clinical and research applications.

Flow cytometry measures targets flowing through an analytical region in a flow cell. In the flow cell a core stream is injected into the center of a sheath flow stream flowing at a constant flow rate. The core stream is a liquid sample, which may be injected from a sample tube. Injection generally requires insertion of an aspiration tube into the sample tube and pressurization of the head above the liquid in the sample tube such that sample liquid is pressure driven from the sample tube into the injection tube.

The flow stream is directed into a tapered portion of the flow cell body and through an analytical region. In one design, the stream is directed through a nozzle and analyzed in air. In a second design, the stream is directed through a channel for analysis.

Analysis takes place by optical interrogation of particles as each particle passes a detection region. In most systems, one or more laser beams are directed by steering mirrors and illumination lenses through the analytical region. If more than one laser are used, a dichroic stack may be used to combine the beams and direct the beams through the stream to be analyzed.

Some of the light passing through the analytical region will be scattered by particles. Detectors measure the intensity of forward and side scatter. In addition, the illumination beam will excite fluorescence from target particles in the flow stream that have been labeled with a fluorescent dye. Emitted fluorescence is collected by a collection lens and transmitted to detection optics. The detection optics separate the collected light (e.g. using filters and dichroic mirrors) into light at specific wavelengths. Light at specific wavelengths, or within specific wavelength ranges, are detected by individual light detection devices (e.g. photomultiplier tubes). The signal from the various detectors is sent to a data processor and memory to record and characterize detection events.

In addition to analysis of particles, flow cytometer systems may also be designed to sort particles. After leaving the optical analysis region, the flow stream may be separated into droplets. One common method of droplet generation is to vibrate the nozzle from which the flow stream emerges. This may be done by vibration of the nozzle alone, or vibration of the entire flow cell. The resultant separated droplets adopt a spacing which is a function of the stream velocity and the vibration wavelength. Droplets containing the target of interest are charged by a charging device such as a charging collar. The charged droplets are directed between two charged deflection plates, which angularly deflect charged droplets. The deflected droplets are then collected in containers positioned in the path of falling deflected particles.

Known flow cytometry similar to the type described above are described, for example in U.S. Pat. Nos. 3,960,449; 4,347,935; 4,667,830; 5,464,581; 5,483,469; 5,602,039; 5,643,796 and 5,700,692. All references noted are hereby expressly incorporated by reference. Commercial flow cytometer products include FACSort™, FACSVantage™, FACSCount™, FACScan™, and FACSCalibur™ systems all manufactured by BD Biosciences, the assignee of the instant invention.

The described system presents a number of advantages for the analysis of particles (e.g. cells), allowing rapid analysis and sorting. However a number of limitations to the system exist.

Alignment

The system requires precise alignment of various elements to function properly. The lasers must be precisely positioned to properly direct light to the objective. To aid in this positioning, the laser or other illumination source is commonly mounted on an x-y-z stage, allowing three-dimensional positioning of the laser. The steering mirrors for the laser beams must be precisely positioned to properly direct the illumination beam to the objective. This generally requires that the mirrors be mounted to allow for angular adjustment. The illumination lens system must be exactly positioned such that the illumination lens focuses the illumination light onto the target area. This lens is also generally mounted such that it can be repositioned along the x-y-z axes.

The flow cell must be positioned such that the angle at which the illumination beam impinges the flow stream and the distance from the flow stream to the illumination lens does not change. Commonly the flow cell is mounted on a stage, which allows x-y-z positioning of the flow cell. In addition the stage holding the flow cell may also allow for angular repositioning of the flow cell (e.g. $\alpha$ and $\theta$ positioning). This angular adjustment is critical for sorting, which requires precise prediction of the sort stream direction. In addition, the optics used for detection of scattered light and fluorescence also must be properly aligned.

The stream in air jet must also be aligned, to ensure that the stream in air is directed in the intended direction. This alignment is effected by angular rotation of the flow cell. This alignment is additionally important if the optical interrogation of the stream takes place in a stream-in-air. The alignment procedure for a stream in air system requires first locating the stream-in-air with respect to both the illumination and the light collection optics and then focusing each of these components on a location within the stream in air.

Alignment requires user time and considerable user expertise. At times it is difficult to determine which element requires adjustment. Set up of the instrument generally requires a diagnostic of alignment with elements realigned by repositioning as needed. This occurs at least once a day, more frequently if an element is replaced or removed. Realignment necessitates both instrument down time and user time and expertise. The time required to perform the alignment procedure is highly dependent on both the condition of the system and the skill of the operator. In addition, the need for constant realignment reduces the repeatability of system performance.

A few attempts have been made to address the problem of the need for repeated alignment of some elements of a flow system. U.S. Pat. Nos. 5,973,842 and 6,042,249 to Spangenberg disclose an optical illumination assembly for use with an analytical instrument. This assembly may include an illumination source (e.g. a laser), a spatial filter, a beam shaping aperture and a focus lens. All elements are illumination optical elements, not the flow cell or light collection elements. Each component is mounted on a plate, frame or mounting cylinder, which in turn are mounted on a platform. Each of the plates or frames is movable along two axes by micrometer adjustments using adjusters with opposing spring plungers. Following an initial adjustment, the plates or frames are secured into a fixed location using screws or other devices to fix the plates or frames into place. The adjusters or springs are removed once the frames or plates are secured. The focus lens would be mounted such that it would be moved along 3 axes (x-y-z movement) and subsequently also be fixed into a location. This allows fixation of the light generation and illumination optics. However, the cuvette would still be adjusted to be positioned at the focal spot of the illumination. This would be required on a routine basis.

U.S. Pat. No. 4,660,971 discloses an illumination configuration in which a focus lens is in contact with a flow cell. A spring biases the lens against a housing, positioning the lens at a selected focal length from the flow cell. This maintains a relative axial position between the lens and the flow cell.

These references, while providing a method in which some of the issues relating to the alignment of the illumination optics are addressed, do not provide a method in which the flow cell and the light collection optics may also be fixed. Fixing all of these elements significantly further simplifies the alignment of the instrument.

Illumination Power

A number of different features in a common flow cytometer setup result in loss of illumination intensity or loss of intensity of collected light. To compensate for these losses generally requires increased illumination power. This requirement for increased power requires expensive and bulky liquid-cooled lasers that provide sufficient power to overcome losses and still allow sensitive target detection. These sources of loss include:

1. Optical interrogation using a stream-in-air. The gross cylindrical geometry of a stream of liquid in air acts as a lens both reflecting and refracting illumination light. This high index of refraction is more pronounced in smaller diameter streams. This refraction makes illumination less efficient and distorts light scatter. To mitigate this effect of scatter distortion an obscuration bar is positioned between the stream in air and the light scatter detector. In some systems, this rectangular obscuration bar may be rotated to block additional amounts of light scatter across a greater area, blocking additional light from narrow angles from reaching the scattered light detectors.

2. Use of dichroic mirrors to combine illumination beams. Each dichroic mirror is not able to perfectly reflect or transmit a light beam. As the beam is reflected or transmitted some light is lost. This loss ranges from 10-20% of beam power (5-10% if beam is reflected; 10-15% loss for transmission through a dichroic mirror), more if the dichroic is not perfectly aligned. A laser beam that is reflected by a steering mirror through two dichroic mirrors to combine three beams could lose 40% or more of the laser's power.

3. Losses in collection of fluorescence. The amount of collected fluorescence can be limited by the optical properties of the flow cell and the collection lens. The geometry of the flow channel and the flow cell define the numerical aperture from which the system is able to collect light. The transition from the flow cell to the collection lens could allow refraction of light and loss of signal as the emitted fluorescence travels through the flow cell, into air, and then into the collection lens. The high index of refraction during material transition results in the loss of collected light. In some systems this loss is mitigated by physical coupling of the flow cell to the collection lens. However, this coupling would be greatly simplified if the flow cell were in a fixed location.

Droplet Generation

Droplet generation has required vibration of some part of the flow cell, generally either the nozzle or the entire flow cell. Vibration of the entire flow cell can result in alignment difficulty as well as additional light scatter created by the vibration. In addition, if the optical analysis is performed in a stream-in-air, the drop-drive perturbations cause undulations on the free surface of the stream. This causes a constant alteration of the light paths into and out of the jet of liquid, making measurement of scatter and focusing of the illumination beam more difficult.

U.S. Pat. No. 6,133,044 provides one alternative to the vibration method of droplet generation. This reference describes a device in which an oscillator is included within the nozzle volume or otherwise is undirectionally coupled to the sheath fluid. The tapering of the nozzle amplifies the oscillations, which are transmitted as pressure waves through the nozzle volume to the nozzle exit. This results in the formation of droplets. The nozzle is directionally isolated to avoid vibration of the entire flow cell or nozzle and limit the oscillations to forming pressure waves in the flow stream.

Optics Positioning Limitations

Ideally, the flow cell would be materially joined to the light collection optics to prevent the loss of collected light. One of the greatest losses of collected light occurs due to the transition between different materials that each have a different index of refraction of light. The light refraction between different materials (e.g. air and glass) may be significant and the resultant light refraction makes the collection and measurement of scattered or fluorescent light difficult. This is mitigated by joining the flow cell to the light collection lens. However for the flow cell and the light collection lens to be coupled by a physical material would require that the two elements remain in a fixed location.

In addition, the need to guard the flow cell from damage (e.g. scratching of surfaces through which light passes) presents another motivation for keeping the flow cell at a fixed location.

Flow Cell Positioning Limitations

Sorting flow cytometers generate a stream of droplets in air and subsequently sort droplets containing target particles. The droplet stream is generated from a flow nozzle positioned at one end of a flow channel. A large degree of uncertainty in the nature of the stream of droplets is a common result, of the way in which the nozzle is located to the flow channel. Most flow designs rely on the "self-aligning" tendency of a female conical structure at the nozzle inlet, which mates with an edge on a cylindrical structure at the flowcell outlet (i.e. the outlet of the flow channel). Typically an o-ring makes a seal between the nozzle conical structure and the flow channel cylindrical structure.

However, there are a few problems inherent with this approach. First, the o-ring has a compliance that aggravates the axial and angular tolerance stack-up associated with locating a conical surface about a circular arc. Second, the angular location of the nozzle about the axis of the flow cell is arbitrary. Third, the angular location of the o-ring about the axis of the flow cell is arbitrary. The first noted problem makes it difficult for a user to duplicate the mounting of the nozzle to a previous mounting configuration. The second and third noted problems make it impossible. Because the angular location of the nozzle and the o-ring are arbitrary, the nozzle is not formally constrained with respect to the flow channel (or the cuvette) through which the flow cell extends.

U.S. Pat. Nos. 6,263,745 and 6,357,307 to Buchanan et al. disclose a nozzle for sorting flat samples. This nozzle seats in a cylindrical recess in the flow cell. U.S. Pat. No. 6,133,044 discloses a removable nozzle for use with a flow cytometer. The nozzle seats in a cylindrical recess in the flow body and is held against a lip. An annular nut secures the nozzle to the body of the tapering flow cell. An o-ring positioned between the nut, the nozzle and the tapering flow cell provides a means for ensuring the axial orientation of the nozzle.

Cell Sorting

Cell sorting requires precise coordination of event detection, droplet generation and droplet tagging. If these procedures become even slightly out of coordination, the incorrect droplets could be charged for sorting or the system could fail to collect the desired particles or cells. For stream-in-air analysis and sorting, this process is simplified because the droplet stream is optically analyzed, droplets are generated and droplets charged all in a stream in air. However, as noted earlier, the stream-in-air sorting produces a decreased signal from cells or particles sorted and the circular stream of liquid can cause both illumination light and scattered light to be reflected or refracted.

Sorting using a system in which analysis is done in a channel also presents challenges. When the liquid moves from an analysis channel and subsequently through the nozzle the velocity of the particles changes, as the liquid flow accelerates at the narrow nozzle. The coordination of flow must account for this change in flow rate.

U.S. Pat. No. 6,372,506 to Norton discloses an apparatus and method for determining drop delay. Drop delay is the time that elapses between detection of a target at an analytical region to the time at which a sorting condition (e.g. a charging potential) is applied to the droplet. As the droplets are formed they are analyzed to determine whether the drop delay is correct. The droplets are analyzed to determine if the target detected at an analytical region is within the droplet to which the sorting condition is applied.

As fluid enters a channel, flow over a short distance can be modeled as "slug flow", all liquid moves as a single front. This would be the case at the entrance of the neckdown region of the flow cell. As liquid moves along the length of the channel, the viscosity of the liquid produces a parabolic velocity profile. The velocity of the liquid flowing through the cuvette channel tube is fastest along the longitudinal axis of the tube. At the walls of the tube the fluid has no velocity. At any intermediate point between the walls and the center of the channel, the velocity of the fluid varies parabolically. This laminar flow results in a spreading of the distance between particles at different distances from the tube center as the particles move through the stream. Particles in the exact center of the stream will move faster than the particles closer to the edges of the stream.

The laminar flow produces a spread of particles as the particles move through the channel. This can make sorting particles optically analyzed in a cuvette channel more difficult. If the velocity of a particle changes as the particle moves through the channel and optical interrogation occurs in the channel, the velocity of the particle at the point of optical interrogation and the velocity of the particle at the point of exiting the channel through a nozzle will be significantly different. Since prediction of the position of the particle depends on knowing the velocity of the particle, sorting particles becomes much more difficult if the velocity of the particle changes.

It is an object of the invention to provide a flow cytometer that requires alignment less frequently, and most preferably only at an initial instrument setup.

It is a further object that this system allows for efficient illumination and collection of light.

It is a further object that the losses of illumination light be reduced to allow for lower power lasers to be used for illumination.

It is a further object to provide a system that is easier to use and provides robust system performance.

SUMMARY OF THE INVENTION

The present objects of the invention are achieved through a number of embodiments of the invention in which elements of a flow cell or flow cytometer system are designed for efficient light collection, efficient droplet production, and minimization of the need for user manipulation of the system.

In one embodiment the invention includes a removable nozzle key, which fits into a registered location on a flow cell at the end of a flow channel. Clogs are an issue: The customer-removable nozzle addresses this with no subsequent alignment required. The nozzle key may be inserted into a registered location on the flow cell such that the nozzle is precisely positioned. The nozzle key may be removed, cleaned, refit into its precise location.

Removal of the nozzle allows the flow cell to be attached at a fixed location on a system platform. If the flow cell position is fixed, other optics that must be positioned relative to the flow cell may also be fixed. This allows the illumination optics, the fluorescent light collection optics and the scattered light detection optics to also be in a fixed location.

The fixed illumination optics may include fixed optics for transfer of the illumination beams into the system and fixed optics for beam shaping and orientation. The optics for bringing the illumination light into the system could use optical fibers coupled into the system at fixed location mounts. The optics for shaping and orienting the beams could be refractive optics, which are less alignment sensitive than the mirrors used in prior systems for beam redirection and shaping.

The light collection optics may also be fixed. If the flow cell is fixed and the light collection optics is fixed, the flow cell may be materially coupled to the light collection lens, as by gel coupling. This lowers losses to refraction.

The design of the present system's elements aids in efficient light collection In one embodiment, the cuvette containing the flow channel has sidewalls extending on three sides of the cuvette below the plane containing the opening of the flow channel. Light emission from the flow channel may pass into the sidewalls and subsequently into the light collection optics. This allows for light collection from a greater numerical aperture than is seen in prior systems. This design also allows the optical analysis to take place quite near the bottom of the flow channel. This makes determination of the drop delay (needed for charging generated droplets for subsequent sorting) simpler. In addition, there is less variability between particles of different velocities. Many of these described features are independent embodiments of the present invention.

In another embodiment of the invention, a flow cell for a sorting flow cytometer is provided in which a removable nozzle is inserted into a registered position in which it is held at a fixed location in relation to the rest of the flow cell. This fixed position prevents the nozzle from either three-dimensional or rotational movement.

Flow cells include a sample delivery tube, at least one sheath flow port, and a channel for optical analysis. This channel may be part of a flow cell body, but preferably is a cuvette joined to the flow cell body. When the cuvette is joined to the flow cell body, the sheath flow and sample stream flows into the cuvette.

Flow cells for a sorting flow cytometer also include a droplet generator. The droplet generator would ether vibrate an element on the flow cell, such as the nozzle, cuvette or flow cell body, or would introduce a oscillating pressure wave within the flow cell body.

The removable nozzle is held on a substrate, such as a card or insertable key, which is fit into a registered position in which the substrate is registered against hard surfaces, allowing the substrate to be removed and replaced into a precise position.

In another embodiment, the sorting flow cell includes an oscillating droplet generator that transmits a pressure wave to the sheath flow fluid flowing through the flow cell. In this embodiment, droplets may be generated without a device for vibrating the flow cell, the cuvette, or the nozzle. A number of noted features, including the registered nozzle, may be included with this embodiment.

In another embodiment, the sorting flow cytometer flow cell includes a flow channel of rectangular cross-sectional dimensions. The shorter side of the channel would face the optical path of the illumination light directed by the illumination optics. The longer side of the channel would face the light collection optics. This configuration has a high numerical aperture for collection of emitted light. The channel may extend through a cuvette. The cuvette may have sidewalls that extend below the area of the nozzle, allowing a wider angle to collect emitted light. This configuration also allows an enhanced numerical aperture of collected light compared to systems lacking the sidewalls. Again, a number of noted features, including the registered nozzle, may be included with this embodiment.

In another embodiment, a flow cell component includes a flow cell for a sorting flow cytometer and light collection lens. The flow cell is joined to the light collection lens by a light transmissive material. In this manner there is no transition into air as light moves from the flow cell to the light collection lens. This reduces the loss due to the change in index of refraction as light moves from the flow cell, into air, and then into the collection lens. In prior non-sorting flow systems, cuvettes could be joined to the collection lens. However, in sorting systems, the need to clear the nozzle and vibrate the flow cell made joining the collection lens and the flow cell inadvisable. In the present invention, these limitations have been overcome, and the advantages of joining the flow cell to the collection lens are achieved.

In another embodiment, the flow cell for a sorting flow cytometer includes a nozzle held at a hard registered location that is off center from the longitudinal center of the channel, this is possible because the nozzle may be removed and reinserted into a precise location. This provides favorable conditions for the formation of droplets and the merger of satellite droplets into parent droplets.

Each of these embodiments represent a component which may be independently produced. Alternatively, each component (flow cell or flow cell with optics component) may be part of a flow cytometer system. Such a system would include light collection optics and illumination light direction optics. The system could also include input optics that would allow illumination light sources to be coupled to the system. Alternatively, the system could be produced with the illumination optics as an already fixed part of the system. In addition, the features of each embodiment may be incorporated with the features of other embodiments if desired.

BRIEF DESCRIPTION OF THE DRAWINGS

FIG. 1 is a perspective view of a flow cytometer system incorporating features of the present invention.

FIG. 2 is a side view of the system of claim 1.

FIG. 3 is a frontal cross section of a flow cell, nozzle and nozzle support platform.

FIG. 4 is a side cross section of the device of FIG. 3.

FIG. 5 is a detail of the nozzle and flow cell shown in FIG. 3.

FIG. 6 is a detail of the nozzle shown in FIG. 4.

FIG. 7 is a detail of the nozzle from FIG. 5.

FIG. 8 is a cross section detail illustrating positioning of the nozzle in the flow channel.

FIG. 9 is a top view of the nozzle card.

FIG. 10 is an exploded view of the nozzle card.

FIG. 11 is a frontal detail view of the light collection optics of FIG. 2.

FIG. 12 is a top view of the nozzle card, flow cell, and fluorescence collection lens.

FIG. 13 is a side cross sectional view of the devices shown in FIG. 12.

FIG. 14 is a perspective view of the devices shown in FIG. 12.

FIG. 15A is a view of droplet formation.

FIG. 15B is a view of droplet formation using the technology of the present invention.

DETAILED DESCRIPTION OF THE INVENTION

In the present invention, significant advantage is derived from a configuration in which a number of the optical elements may be fixed with respect to the flow cell. This advantage arises from the extent of directional stability afforded by the nozzle, which the user may remove and replace and which is self-aligning. The nozzle is insertable in the flow cuvette at a location where the nozzle is registered in place. This registration allows the nozzle to be inserted and positioned such that the nozzle is constrained both as to translation and rotation. Because only the nozzle is movable, the flow cell may be fixed, and does not need to be positioned on a stage that may be angularly or directionally repositioned. As a result, no removal or replacement of the flow cell is required and the user will not have to adjust or realign the flow cell assembly to align the stream of droplets with a required direction for sorting.

Because the flow cell and flow channel never need to be moved, the other optical elements that must be focused or positioned relative to the flow cell now may be fixed as well. This fixation may be location of the flow cell on one fixed plate and the location of other optical elements on one or more additional fixed plates, with each plate in a defined positional relation to any other plate. Alternatively, the flow cell could be materially linked to other optical elements, such as by physical joining of the flow cell with the collection optics. Materially joining the flow cell to the light collection optics allows reduction of the index of refraction between material transitions and allows more efficient collection of light.

The present configuration minimizes tolerance stack-up. Only the fabrication tolerances of two mating elements, the nozzle and the receiving flow cell body can contribute to the stack-up. These are the only two elements that would be moved in relation to the other. An intermediate locating element between the nozzle and the cuvette would, at least, double the tolerance stack-up and adversely affect stream stability.

With reference to FIGS. 1, 2 and 11 the system allowing fixed position mounting of the elements is shown in a perspective view. The lasers (not shown) produce illumination light, which is directed through an optical fiber, linked to the system by mounts. The first, second and third optical fiber mounts 11, 12, and 13 respectively each receive an optical fiber bringing illumination light from one laser. Optical fiber mounts are mounted on plate 19 that is secured to platform 20 by braces 22. Braces 22 ensure that plate 19 will be maintained in a fixed position. Light from optical fibers coupled to mounts 11, 12, and 13 is directed through illumination refracting optics.

A series of prisms are used to combine the illumination beams into illumination light having specific properties. At the point of illumination, it is preferred that the illumination beams be elliptical, concentrating the illumination energy at the central location of the core of the flow stream. As the light is directed through prisms 23, 24, 25 and 26 the illumination beams are differentially refracted by the prism such that the illumination beams are redirected and aligned at the illumination location within a flow cell. Prisms 23, 24, 25 and 26 are mounted on plate 21, which is secured to platform 20 by braces 27. The mounts for both the laser couplings and the prisms may be adjusted once at the setup of the system, positioning each element in a fixed location. This may be performed by either adjusting the mounts for each element, or repositioning the plate on which elements are mounted so that a number of elements are moved together. The prisms are less sensitive to angular misalignment and are more thermally stable. Both of these features aid in allowing set position of this element.

The illumination beams pass through the illumination beam combining optics and through illumination lens 30 held in illumination lens mount 31. Illumination lens mount 31 is positioned on arm 60 secured to face 61 on lens positioning stage 33. Micrometer 35 extends to arm 60 to allow movement of lens mount 31 along the z-axis. Plate 61 is movable by micrometer 34 to allow movement of the illumination lens mount along the y-axis. Micrometer 36 is mounted through lens positioning block 33 to allow movement of lens mount 31 along the x-axis. In combination, positioning micrometers 34, 35, 36 allow lens mount 31 to be repositioned in the x, y, and z directions. Lens mount 31 is mounted on block 33, which is mounted on platform 20. Plates 19 and 21 and block 33 are each at a separate location on platform 20. Each of these elements may be separately adjusted initially at installation for alignment.

The focused illumination beams pass through the illumination lens held in lens mount 31 and through the optical analysis region of the flow channel in flow cell 41. As particles pass through the flow channel and cross the illumination light beams, light will be scattered and fluorescence will be excited. Scattered light will be detected by forward light scatter detector 43. Emitted fluorescence as well as large angle scattered light will be collected by emission collection optics. Flow cell 41 and forward light scatter detector 43 are mounted on plate 39. Plate 39 is held on platform 20 by brace 29. Platform 20 is supported on feet 46. Isolation mounts 45 allow mounting of platform 20.

In the system of FIG. 1, the optics for bringing in light, redirecting the beams into the desired illumination orientation, collection of the scattered and emitted fluorescence are all held in a fixed position. In addition, the flow cell is also held in a fixed position. These elements are each mounted on a plate and need to be aligned initially when the instrument is installed. Routine realignment of these elements will not be required. The illumination lens could be routinely realigned. However, alignment of a single element greatly simplifies the time and difficulty of alignment.

It should be realized that a number of the elements of this system have independent utility. For example, simply having a fixed location flow cell and light collection optics allows joining of the flow cell to the collection lens to more efficiently collect illumination light. Fixing the mount location of the beam redirection optics also saves user time and provides a method of combining illumination beams into a single illumination beam without using mirrors (and the attendant loss of light characteristic of mirrors).

The term "fixed location" as used herein refers to an element which does not have a means for user adjustment. This element at a fixed location would be aligned initially (generally at instrument set up) and not require further alignment.

"Illumination input optics" refers to optical elements that allow introduction of light to a system (e.g. optical fiber mounts).

"Illumination beam directing optics" are optical elements that redirect and reshape the illumination beams (e.g. serial prisms). Illumination beam directing optics may or may not include a focus lens.

"Light collection optics" refers to optical elements disposed to collect emitted or scattered light from the flow channel. In flow systems such optics generally include a fluorescence and wide angle scatter collection lens and a forward scatter detector.

The ability to have a fixed position illumination input optics, illumination beam directing optics, flow cell, and light collection optics depends on two factors. The first is the ability to direct light with elements that will not routinely go out of alignment. The second is the ability to fix the location of the flow cell, allowing the distance between the flow channel, the illumination optics and collection optics to remain constant. This allows the illumination optics and the collection optics to also be located at fixed locations. It further allows the flow cell to be joined to the light collection optics in a way that minimizes loss of the collected light.

With respect to FIGS. 3 and 4, the flow cell 41 is shown in front and side cross section respectively. The sheath flow tubes are not shown in these views. Generally sample delivery tube would be positioned such that the sample is introduced just before the neckdown region (the region adjacent to the beginning of the flow channel) as shown in FIG. 3. The two sheath flow delivery tubes provide sheath flow in an even, pulse free flow.

In FIG. 3, the flow cell 41 is shown comprised of flow cell body 230, cuvette 210, nozzle key 214, and flow cell base plate 220. Flow cell body 230, cuvette 210 and flow cell base plate 220 are joined together to form a single unit that may be secured in a fixed location by bolts extending through holes 209 onto a flow cytometer instrument (e.g. by bolting the flow cell onto a fixed position plate). The nozzle key 214 is not fixed and may be inserted into a location such that the nozzle is at the end of the flow cannel. The nozzle key could be subsequently removed, cleaned (e.g. sonicated) and reinserted. In addition, the fitting 233 containing the sample input tube also might be periodically removed and reattached. This allows the remaining portions of the flow cell to be in a fixed location within a flow cytometer.

The upper portion of the flow cell is the flow cell body 230, which receives both the sheath flow tubes and the sample delivery tube 202. The sheath flow liquid is delivered in tubes joined to fluid input body though ports 206, 208. The flow is delivered such that the sheath fluid surrounds a core of the sample stream as liquid passes through the flow channel 212. The sheath fluid carries the core stream through a converging channel in flow cell body 230 and into the flow channel 212 in cuvette 210.

The flow cell body 230 has an open top end through which the sample tube and oscillator are introduced. Inserted through the open top end is sample tube inlet fitting 233 and transducer plunger 232. Plunger 232 is retained on boss 202 on flow cell body 230. A tube (not shown) held by fitting 233 introduces a sample liquid through a passage in fitting 233. This passage is joined to sample delivery tube 202 such that liquid flows through the passage, into sample delivery tube 202 and into a passage within the flow cell body. The sample delivery tube 202 terminates at an open end proximate to the flow channel 212 that extends through cuvette 210. At this location the sample flowing through sample delivery tube 202 is surrounded by sheath flow fluid, forming the sample into a core in the flow stream as the stream moves through flow channel 212.

The flow stream flows through flow channel 212 in cuvette 210 and exits at nozzle 216. The length of flow channel H1 is sufficiently long to ensure fully developed flow in the optical analysis region H2 under all operating conditions. In the illustrated system a length of 8-15 mm is sufficient for a fully developed flow. Sidewalls 213 extend about three sides of nozzle key 214, allowing registration of the nozzle key 214 in place. At the point of exit, the sample stream flow velocity increases as the sample exits 15, the narrower nozzle opening.

Nozzle 216 is mounted on nozzle key 214, positioned at a registered location at the end of cuvette 210. The bottom side of nozzle key 214 rests on flow cell base platform 222 on flow cell base plate 220. H1 indicates a height of the cuvette between the flow cell body 230 and the nozzle key 214. This is the location where illumination beams are directed through flow channel 212. Close tolerances between the nozzle and the registration features insure that the direction of the stream does not change after a nozzle has been removed and replaced by the user.

FIG. 5 shows a detail of the nozzle key 214 and cuvette 210. Nozzle key 214 has a nozzle key card 213 affixed to the top surface of the nozzle key 214. The nozzle 216 is positioned on nozzle key card 213 on the nozzle key 214 such that the nozzle 216 is positioned at a selected location in the cross section of flow channel 212 when nozzle key 214 is inserted into cuvette 210. When nozzle key is inserted into the registered position, nozzle key 214 is held between flow cell base platform 222 and the top surface of cuvette. The stream generated by flow through nozzle 216 flows into passage 218.

The detail of the nozzle is shown in FIG. 7. Cuvette 210 is shown having a flow channel 212. At a terminus of flow channel 212 nozzle 216 is positioned. Nozzle 216 is shaped like a truncated funnel, producing a more stable flow stream. On nozzle key card 273, an annular groove 261 holds an o-ring 260. O-ring 260 seals nozzle key card 273 to cuvette 210 when nozzle key 214 is inserted in its registered position.

With reference to FIG. 3, the stream in air which flows from nozzle 216 then passes through passage 218. The sample could be collected here or the stream could be separated into droplets, allowing subsequent charging and sorting of droplets. To generate droplets, a drop drive piston 240 may be used. Signals for the power and operation of the drop drive piston 240 may be sent through transducer electrical terminal 235. The electronic signal is sent to drop drive piezo element 234 held in transducer plunger 232. Drop drive piezo element 234 oscillates drop drive piston 240, sending oscillating pressure waves through the incompressible sheath flow fluid.

Previous systems have used vibration (as from a piezoelectric crystal) of the nozzle cuvette, or flow cell to generate droplets. The droplets generated are separated by the wavelength of the vibration. This allows division of the flow into individual droplets for sorting. However, the vibration of either the nozzle or the entire flow cell could have negative effects on the consistency of illumination and light collection if the vibration causes the relative distance from the flow channel and the illumination focus or light collection focus to change. This effect is more pronounced in stream-in-air optical interrogation. In the present invention, droplet generation originates from a displacement type oscillator near the source of the sheath flow. It has been found that the pressure waves are transmitted through the largely incompressible flow fluid and effectively generate the desired droplets.

With respect to FIG. 4, the side cross-section shows detail of the key nozzle 214 as it is secured in place. In the side view, key 214 is shown having nozzle key grip 270. Nozzle key 214 has a passage 218 defined by surface 254 and surface 256. Nozzle key plunger 281 biases the nozzle against the sidewall of the cuvette, holding the nozzle in a registered position. The detail of the nozzle section shown in FIG. 6 shows the insertion of the nozzle between cuvette 210 and flow cell base platform 222, holding nozzle key 214 in a position such that nozzle 216 is registered against the terminus of channel 212 extending through cuvette 210, by the cell base platform 222. Nozzle key plunger 281 provides a biasing pressure to retain nozzle key 214 in position. Shoulder 311 on nozzle key 214 is appressed against a surface of cuvette 210 when the nozzle key is fully inserted. This positions the nozzle at a registered position. The nozzle is prevented from being inserted too far, preventing damage to back wall 254.

The details of the nozzle key are shown in FIGS. 9 and 10. In FIG. 9, nozzle key 214 is shown with nozzle 216 positioned on nozzle key card 273. Label 271 affixed to the bottom of the card allows identification of the specific nozzle card used. Nozzle key plunger 281 provides a biasing force of the nozzle key 214 against the side walls of cuvette 210. Nozzle key grip 270 allows a user to grip nozzle key 214 and remove it from cuvette 210. In this way if the nozzle were to become clogged, the nozzle could be simply removed, cleaned (e.g. sonicated) and replaced.

In FIG. 10, the nozzle key is shown in exploded view. The nozzle key plunger 281 is inserted through the nozzle key 214. Spring 282, retained within nozzle key 214 by nozzle key spring plug 283, provides a biasing force on plunger 281. Plug 283 is retained on plug retainer 284.

Nozzle key card is affixed on the top of nozzle 214. O-ring 260 fits into groove 261 to provide a sealing force of the key card 273 to the cuvette when nozzle key 214 is inserted into the cuvette.

The use of a cuvette for the optical analysis of the stream allows for a lower excitation power requirements and greater efficiency of the collection optics. As opposed to analysis in a stream in air, the cuvette presents a stationary target with a flat interface for the incoming laser light from the illumination optics. Therefore, less light is lost to reflection and refraction. Because less light is lost, lower laser power is required. These features also make the collection of light more efficient. Less light is lost due to refraction of light from the stream to the light collection optics. In addition, the material transition from the stream to the collection optics can avoid the transition from liquid to air, with the attendant high index of refraction eliminated.

As noted in respect to FIGS. 1 and 2, the use of the nozzle that may be inserted into a registered position allows fixing the position of the flow cell, illumination optics and the light collection optics. One advantage to this configuration is the elimination of wear and tear on the flow cell. When the flow cell is removed, it is possible that the surfaces through which light pass on the flow cell could become scratched or marred such that light collection or transmission to or from the illumination channel is altered. This is mitigated by fixing the flow cell in place and not requiring the flow cell to be moved or manipulated.

As noted, each material through which light passes will have a characteristic index of refraction. Light will be refracted when it passes from a medium having a first index of refraction to a medium having a second index of refraction. A major problem encountered in prior systems that optically analyze in a stream in air is the high index of refraction between the stream of liquid, and air. This, coupled with illumination light losses due to the gross cylindrical nature of the stream in air, requires higher excitation power than is required in a cuvette system.

In a cuvette system, losses to refraction also occur in the transition from the cuvette to air material transition as emitted fluorescence moves from the cuvette, into air and subsequently into the collection lens. Fluorescence excited in a liquid moving through the flow channel is collected by a collection lens on one side of the flow channel. If the flow cell is fixed in location, the light collection optics may be physically joined to the cuvette. This reduces the refraction at the material transition from the cuvette to the collection lens.

With reference to FIGS. 12 and 14, the cuvette 210 is joined to the emission collection lens in housing 50. The nozzle key 214 is inserted into position such that the nozzle is positioned at the end of the flow channel. This is shown in FIG. 13. In this cross sectional view, the flow channel 212 is shown extending through the cuvette 210. The cuvette 210 is linked to an initial optical element 52 by a gel 290. Light is collected by lenses in housing chamber 51. One such collection lens is disclosed in U.S. Pat. No. 6,510,007, entitled "Flow Cytometry Lens Systems".

Nozzle key 214 is inserted and registered against cuvette 210. In one direction this registration is effected by biasing the key by nozzle plunger 281, holding the nozzle card in position laterally.

The sidewalls 213 of the cuvette 210 extend below the exit plane of the cuvette (i.e. the plane containing the exit of the end of the flow channel). This allows for a larger numerical aperture $\alpha$ for the collection of emitted fluorescence and for forward scatter. In addition the lower sidewalls 213 permit a lower entrance point for the laser beams, enabling the closest possible location of the optical interrogation region to the nozzle. In one embodiment the optical interrogation is 700 nm from the nozzle opening. This configuration ensures minimization of the delay time and least time delay error between the lowest laser illumination of the stream (target detection) and the droplet charging.

In prior flow cytometers in which optical analysis of a sample occurs in a cuvette channel, the cuvette would be of a block shape and the sidewalls would terminate at a bottom surface of the cuvette. In this configuration the illumination must occur a significant distance from the bottom of the cuvette, in order for efficient light collection of emitted fluorescence. If illumination occurs too close to the bottom of the cuvette, much of the potentially collectable fluorescent light will be lost from the bottom of the cuvette, which would refract the light away from the collection lens. To avoid this problem, the light collection would occur a significant distance from the bottom of the cuvette and thus a significant distance from the end of the flow channel. This may be acceptable for non-sorting applications, but for sorting applications the separation distance of the detection of targets and the nozzle is critical for determining drop delay and properly charging and deflecting droplets of interest. It is also critical towards avoiding time delay errors, which reduce sorting performance.

In addition to the lower sidewalls, the geometry of the channel also allows for more efficient illumination and light collection. In the present illustration, a rectangular cross sectional channel is used. The shorter side of the channel faces the illumination light and the longer side of the channel faces the collection lens. This allows collection from the area of the longer side of the channel. This presents a higher numerical aperture for collection. In FIG. 8 this is indicated by angle $\alpha$. Collection from a higher numerical aperture allows more efficient collection of emitted light and greater sensitivity. This greater sensitivity enables use of lower power lasers. In addition, this wide viewing window allows keeping the cross-sectional area relatively small. This reduces the volumetric consumption of sheath flow required for the system.

The system shown in FIGS. 1 and 2 would be contained in a housing (not shown). This housing would prevent light from the area surrounding the system from entering the system.

Sorting droplets requires precise coordination of the detection of a target of interest, encapsulation of the target into a droplet during droplet formation, charging the droplet and sorting the droplet by passing the charged droplet containing the target of interest between two charged deflection plates. The flow of fluid into the flow cell is kept pulse free so that the perturbations of the fluid are minimized. This allows the general condition of directional stream in air stability.

It is desirable to have the flow stream break up into droplets in a predictable manner. In a sorting flow cytometer, the drop drive causes a leading order effect in which the flow stream-in-air, after flowing from the nozzle, breaks into a train of large droplets having a characteristic diameter of the same order of magnitude as the jet diameter, as shown in FIG. 15a. Due to the nonlinearity of the fluid dynamics characteristic of flow cytometry, smaller droplets 306a typically form between the larger "parent" droplets 304a. The smaller droplets are referred to as "satellite droplets". It is advantageous to have a stream condition in which no satellites form, or in which the satellite droplets that do form quickly merge into the parent droplets. The satellite droplets are significantly smaller, and hence have lower masses, than the parent droplets.

During particle sorting, sorting is accomplished by selectively charging droplets. The droplets then pass through an electric field that deflects the path of the charged droplets so that the charged droplets are deflected from the rest of the droplet stream. The deflected droplets are deflected into a separate collection container for later use or analysis. The required magnitudes of both the droplet charging and electric field potentials of the charging plates are selected to provide the needed deflection of the parent droplets. The smaller satellite droplets that are deflected by the charged deflection plates may be so light that the particles are directed out of the flow stream and onto the charging plates. The resulting wetting of the charging plates may adversely affect system performance and require interruption of the use of the system to dry and clean the deflection plates. In addition, the deflection of satellite droplets could present biohazard risks, especially if the satellite droplets form aerosol droplets that remain suspended in the air.

In the prior systems, favorable satellite conditions were achieved through trial and error. A user could make ad hoc adjustments to the drop-drive amplitude, drop-drive frequency, and sheath pressure until a favorable satellite droplet conditions are achieved (i.e. satellites quickly merged with parent droplets). This is largely guesswork, requiring a knowledgeable user and some time. Optical systems that monitor droplet formation are required to determine that the satellite droplets are merging with the parent droplets.

Theoretically, a perfectly symmetric jet excited near its spontaneous drop frequency will break into a droplet chain whose satellite droplets never merge with the parent droplets. A portion of the drop drive energy cascades into a secondary satellite droplet formation harmonic, in phase with the fundamental droplet formation frequency. Some experiments have shown that one method to control the satellite formation is to add a phased, higher-harmonic component to the drop drive vibration or pulsation to alter or cancel satellite development. (see Chaudhary, KC, and Redekopp, LG, "The nonlinear Capillary Instability of a Liquid Jet. Parts 1-3" J. Fluid Mech., Vol. 96 (1980a-c)).

Location of the nozzle in a precise location in relation to the flow channel allows creation of a repeatable and favorable satellite droplet merging conditions. One embodiment of the present invention uses the nozzle location to ensure more optimal satellite droplet merging. With reference to FIG. 8, a detail of the cross section of the cuvette 210 shows the flow channel 212 with a circle indicating the nozzle opening 294. The center 292 of nozzle opening 294 is positioned off center from the cross sectional center of flow channel 212. A small lateral adjustment of the centering of the nozzle in the flow channel provides a more favorable condition for merger of the satellite droplets with the parent droplets.

In one embodiment of the invention the nozzle is purposefully misaligned with respect to the center of the flow channel. This misalignment may be achieved by machining 0.001 inch from the nozzle registration feature that locates the nozzle in the long dimension of the cuvette channel (e.g. the sides of the nozzle card). The present system allows precise location of an insertable nozzle card. The ability to precisely and repeatably locate the nozzle allows design of the nozzle card such that the nozzle is off from the flow channel center.

The nozzle location is fully constrained by hard features on the nozzle that register directly against the cuvette (or flow cell) such that the nozzle orientation is always fixed in three dimensions with respect to the exit of the cuvette channel. The registration of the nozzle in this manner minimizes tolerance stack up. The limiting factors of this approach are the manufacturing tolerances associated with manufacturing the nozzle and the cuvette. State of the art manufacturing procedures allow nozzle location to +/−0.0012" (+/−30.48 μm) in the plane of the channel. Given these manufacturing tolerances, nozzle-to-nozzle stream performance has proven to be consistent. A given nozzle will always register against a given cuvette in the same manner, ensuring a consistent stream direction and droplet formation pattern.

As noted, the theoretical model of droplet formation indicates that an axisymetric flow stream excited by a fundamental frequency in the range of the spontaneous droplet frequency will break up into a droplet chain in which the satellite droplets never merge with the parent droplets. This implies that deviation from perfect axisymetry could allow for more optimal satellite droplet merging conditions.

In the present illustration, the nozzle is adjusted laterally in the long dimension. This is generally preferred, as it produces the smallest variation in the path for particles within the flow stream. This minimizes the difficulty in timing the delay between detection in the channel and charging and sorting droplets after the droplets have passed through the nozzle. It is also possible to have the displacement in the shorter dimension or displace the centering in both the long and the sort dimensions (i.e. displace on a diagonal from the cross sectional center of the stream).

With reference to FIG. 15a, an image of the stream shows droplet formation in a system in which the center of the nozzle opening is closely aligned with the center of the flow channel. At the top, the stream has begun to break into individual droplets. Height A marks the distance from the formation of the first droplet broken from the flow stream to the area where the satellite droplets have combined into the parent droplets. It would be preferred that droplet deflection not occur before this location. Parent droplet 304a and satellite droplet 306a are identified close to the location of droplet formation at the top of height A. A merging parent and satellite droplet 305a are identified close to the bottom of height A. Eight or more droplet wavelengths are required before the parent droplet and the satellite droplets have merged.

With reference to FIG. 15b, an image of the droplet formation pattern in which the nozzle has been misaligned is shown. This is the misalignment shown in FIG. 8, in which a rectangular flow channel is used. The dimensions of the flow channel in this embodiment is 250 um by 160 um. The nozzle is deliberately shifted 25.4 um off of the centerline of the cuvette in the long axis of the cuvette. In FIG. 15b, height B is a height from the location of a droplet formation to a location where the droplets do not show any satellite droplets. Satellite droplet 306b, shown just after droplet break-off point, and parent droplet 304b are shown. A merging parent droplet with a satellite droplet 305b is just below. In three droplet wavelengths the parent droplets have merged with the satellite droplets.

It will be readily appreciated by a person of ordinary skill in the art that a number of modifications to the present invention are possible. The nozzle opening, as presently illustrated, is a truncated tapered cone. A card is affixed to a nozzle key such that the nozzle is in a precisely registered location when the card is inserted into the flow cell. The nozzle may take many shapes and geometries. For example, an elongate nozzle opening may be preferable in some applications to a round opening. The nozzle may be a lengthened truncated cone, extending downstream from the flow stream direction. In this way the transition from the width of the flow channel to the nozzle may be made less abrupt, and could be a continuous graded tapering to the nozzle opening. In addition, the substrate on which the nozzle opening is formed may use a number of different designs.

A number of the elements of the present invention could be used independently or in a number of different combinations. The fixed flow cell with nozzle key may be adapted into present systems in which the illumination optics and light detection optics may be aligned. Alternatively, the fixed flow cell may be used with either fixed location light collection optics (e.g. fluorescent light collector and light scatter collectors) or a fixed location illumination optics. Other optical elements within such systems would still require routine adjustment. Such systems would retain the advantage of having a fixed position flow cell that does not require to be removed or adjusted. In some embodiments, the cuvette may not be physically coupled to the light collection optics. Such embodiments could have all of the attendant optics (illumination optics, light collection optics, and scatter detection optics) in a fixed location or have some or all of these elements mounted on an adjusting mounts.

The droplet drive may be generated by an oscillator within the flow cell, allowing transfer of the oscillating pulse to the largely incompressible fluid. Alternatively, the droplet drive may be generated by more conventional means, such as vibrating the nozzle, cuvette or vibrating the entire flowcell assembly. Additionally, the droplet drive may be generated by acoustic vibration of the stream in air.

In the illustrated embodiment, the flow cell body is joined to a rectangular cuvette and the nozzle is inserted at the terminus of the cuvette. The term "cuvette" in various embodiments, is the flow cell section through which the channel extends. This may be a separate component joined to a flow cell body. Alternatively, the cuvette may be part of the flow cell body, which may be manufactured as a single part.

In the preferred embodiment, the nozzle is on a substrate that is inserted into a fixed position where it is registered against surfaces to hold the nozzle in a three-dimensional position such that the nozzle cannot angularly rotate. This allows the cuvette and flow to be in a fixed position. Because the channel is in a fixed position, the illumination optics and light collection optics may also be in a fixed position. In addition, the cuvette may be physically joined to the collection lens. It is also foreseen that a flow cell could be made in which the nozzle is a fixed part of the cuvette and the cuvette and nozzle are removed and inserted together. Precision guides could be used to precisely position the cuvette at the required location needed for alignment with illumination optics. The cuvette could be removed, sonicated or otherwise treated to clear a clog in the nozzle or flow channel, and replaced into a precise position. Because the droplet generator is in the flow cell body, the cuvette and nozzle could be removed and reinserted without having to reconnect to a vibration generator.

The invention was illustrated in a system in which multiple lasers are directed into the system using optical fibers. The beams are redirected and shaped using refractive optics. It is envisioned that a single laser or any number of lasers may be used. The lasers could be positioned on the platform and held in a fixed position (e.g. using diode lasers). It is also possible to employ non-laser light sources such as arc lamps. In place of the refractive optics, the conventional use of steering mirrors and dichroic mirrors could be used to direct and shape the illumination beams. In addition, spatial filters, long or short pass filters, apertures or other optics may be employed to block stray light and reduce transmission of undesired wavelengths. Systems employing conventional optics are disclosed in the references cited herein, which are collectively incorporated by reference.

The flow channel in the present illustration is rectangular. In other embodiments, a round flow channel or other geometries are envisioned. In the illustrated embodiment, nozzle is on a removable key. However, the nozzle could also be precision aligned and affixed (by sonic welding, adhesive attachment, etc.) to the end of the flow channel. Such a system would require some means of back-flushing the nozzle to clear clogs.

The illustrated system discloses the use of the flow cell in a sorting flow cytometer. While the present invention provides numerous advantages when employed in a sorting cytometer, it is also considered that disclosed technology could be used in non-sorting analytical cytometers.

The interior of the flow cell could be coated to prevent adhesion of cells, cell fragments or other compounds. Such a treatment would be selected to not be affected by the flow fluid. The flow cell is not removed but may be selectively flushed. The sheath flow system may be designed to allow for system flushing. If fluid is introduced through a first sheath flow port and removed through a second port, flow conditions would direct the flow in a vortex through the flow cell interior, washing all elements.

Because the nozzle is smaller than the flow channel, any clog is likely to occur in the nozzle, which may be removed and cleaned. If the channel clogs, the nozzle may be removed and the channel cleared with back pressure.

The present invention allows development of a system in which the user does not have to perform any routine optical alignment procedure. The user could remove and replace the nozzle without further alignment of the stream direction or optics. The analysis is effected in a cuvette, with the attendant sensitivity allowed by analysis in a cuvette. Sorting occurs in the steam in air, allowing sorting in the conventional manner. The relatively low velocity of the core stream in the analysis region is advantageous for analysis of targets. The stream is then accelerated by the nozzle, to allow for high speed sorting. These advantages present a considerable cost savings due to both time saved as well as skill required to use the system. This system also significantly improves the depth and sensitivity of analysis and sorting performance.

What is claimed is:

1. A sorting flow cytometer system comprising:
   (a) a flow cell, wherein said flow cell comprises:
      a flow cell body;
      a sample delivery tube extending into the flow cell body;
      at least one sheath flow port on said flow cell body, said at least one port allowing introduction of sheath flow liquid through said flow cell body;
      a cuvette having flat sides, joined to the flow cell body;
      a channel extending through said cuvette, said channel comprising an initial end and a terminal end, wherein liquid from said sample delivery tube and said at least one sheath flow port flows into said initial end of said channel flows out of said channel at said terminal end; and
      a nozzle at said terminal end of said channel having a single nozzle opening, wherein said nozzle opening is off center from a centered position within the channel;
   (b) a droplet generator associated with said flow cell body, said droplet generator allowing production of droplets from a stream exiting said nozzle;
   (c) illumination optics that focus and direct illumination light into said channel at an illumination region;
   (d) detection optics that collect light emitted from said channel, wherein said detection optics comprise a light collection lens positioned adjacent to a side of said cuvette; and
   (e) a coupling material joining said light collection lens to said cuvette, said coupling material allowing emission light to pass from said cuvette to said light collection lens without a transition into air.

2. The system of claim 1, wherein said droplet generator imparts an oscillating force to fluid in said flow cell body without direct vibration of the flow cell body or the nozzle.

3. The system of claim 1, wherein said coupling material is a gel material.

4. The system of claim 2, wherein said droplet generator includes a piston.

5. The system of claim 1, wherein said cuvette has optically transmissive sidewalls that extend downward from a location of said terminus of said channel.

6. The system of claim 1, wherein said channel has a rectangular cross section.

7. The system of claim 1, wherein said channel is rectangular and has a shorter cross-sectional side and a longer cross-sectional side, wherein said shorter cross-sectional side faces a first direction in which light is directed by said illumination optics and said longer cross-sectional side faces a second direction from which emitted light is collected by said detection light collection optics.

8. The system of claim 1, wherein said channel has a length sufficiently long so that liquid flowing through said channel has fully developed flow when said fluid reaches said illumination region.

9. The system of claim 1, wherein said channel has a length at least about 8-15 mm.

* * * * *